US006379615B1

(12) United States Patent
Ogle (10) Patent No.: US 6,379,615 B1
(45) Date of Patent: Apr. 30, 2002

(54) METHODS OF STERILIZING ARTICLES

(75) Inventor: Matthew Frank Ogle, St. Paul, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/512,123

(22) Filed: Feb. 24, 2000

(51) Int. Cl.$^7$ ................................................. A61L 2/00
(52) U.S. Cl. .............................. 422/28; 422/34; 422/1; 424/405
(58) Field of Search .................... 422/28, 34, 1; 549/512; 564/503, 297, 320; 424/405; 514/1

(56) References Cited

U.S. PATENT DOCUMENTS

| | | |
|---|---|---|
| 3,278,561 A | 10/1966 | Gaertner |
| 3,956,502 A * | 5/1976 | Slovinsky et al. ........... 424/304 |
| 5,813,452 A * | 9/1998 | Haruta et al. ............... 165/133 |

FOREIGN PATENT DOCUMENTS

| | | |
|---|---|---|
| EP | 0 199 247 A | 10/1986 |
| WO | WO 92/09309 | 6/1992 |

OTHER PUBLICATIONS

"Disinfection, Sterilization and Preservation" by, Seymour S. Block, Ph.D., Lea & Febiger, 1991, pp. 1050–1051 & 1060.

"Kinetics Of The Reaction of N,N,N', N'–Tetraglycidylhexamethylenediamine And N,N,N–Triglycidylamine With Active Centers of Gelatine" by, Mart'yanova et al., USSR. Sb. Nauch. Tr. Leningr. In–t Kinoinzh, Issue 2, 1990, pp. 139–141. Abstr. No. 6L685.

"Kinetics Of The Reaction of N,N,N', N'–Tetraglycidylhexamethylenediamine And N,N,N–Triglycidylamine With Active Gelatine Centers" by, Mart'yanova et al., USSR. Sb. Nauch. Tr. Leningr. In–t Kinoinzh, Issue 2, 1990, pp. 139–141. Abstr. No. 12N270.

"Production of N,N,N–Triglycidylamine" by Chezlov et al., USSR, Zh. Prikl. Khim. (Leningrad) (1990), 63(8), 1877–8., Coden Zpkhab; ISSN: 0044–4618.

"Some Reactions of Epichlorohydrin With Amines" by, Ross et al., The Journal of Organic Chemistry, vol. 29, Jan.–Apr. 1964, pp. 824–826.

"Structure and Reactivity of Oxirane–Type Chemical Modifiers For Gelatin" by, Chezlov et al., St. Petersburg. Inst., Kino Televideniya, Zh. Prik Khim. (1998), vol. 71(1), pp. 149–156, Coden: Zpkhab; ISSN: 0044–4618.

* cited by examiner

Primary Examiner—Krisanne Thornton
(74) Attorney, Agent, or Firm—Hallie A. Finucane; Patterson, Thuente, Skaar & Christensen, P.A.; Peter S. Dardi (57) ABSTRACT

Approaches are described for sterilizing medical and biological articles using sterilizing compositions. The sterilizing compositions include epoxy amine compounds and, optionally, alcohol. The epoxy amine compounds act as antimicrobial agents in the sterilizing compositions. In particular, medical articles can be sterilized and/or stored in the compositions described.

33 Claims, 4 Drawing Sheets

FIG. 4

METHODS OF STERILIZING ARTICLES

BACKGROUND OF THE INVENTION

This invention relates to treatment of articles using sterilizing compositions. More particularly, this invention relates to the use of chemical sterilants for sterilization of articles.

Articles used in biological and/or medical procedures are sterilized to significantly reduce or eliminate the number of potentially contaminating microbes associated with the biocompatible articles. Contaminating microbes associated with articles can lead to failure of biological and/or medical procedures. In particular, microbial contamination in medical procedures can lead to serious health risks.

A variety of biocompatible medical articles are designed particularly for contact with a patient's bodily fluids. The duration of this contact may be relatively short, as is typical with wound dressings, or may be long term, as is typical with prosthetic heart valves implanted into the body of a recipient. Some articles such as catheters can have either short term or relatively long term contact. Other articles typically having relatively short term contact with the patient include, without limitation, burn dressings, contact lenses and surgical instruments. Other articles typically having long term contact with a patient include, without limitation, prostheses.

Contact of articles with bodily fluids creates a risk of infection. This risk can be very serious and even life threatening. In addition, considerable costs, and longer or additional hospital stays, may result due to infection. For example, infections associated with dressings can increase the seriousness of the injury for burn victims. Also, infection associated with an implanted prosthesis can necessitate replacement of the device. Thus, there is a need for sterility assurance in these articles.

Infections are a particularly common complication resulting from the use in hospitals of percutaneous devices such as catheters. Infections related to catheter use can result from intracutaneous invasion during catheter insertion or from invasion by way of the exit site during use. Adherence of bacteria to the catheter surface complicates treatment of the infection.

Prostheses, i.e., prosthetic articles, are used to repair or replace damaged or diseased organs, tissues and other structures in humans and animals. Prostheses generally must be biocompatible since they are typically implanted for extended periods of time. Examples of prostheses include, without limitation, prosthetic hearts, prosthetic heart valves, ligament repair materials, vessel repair and replacement materials, and surgical patches. Many prostheses incorporate tissue as at least a component of the prosthesis.

Physicians use a variety of prostheses to correct problems associated with the cardiovascular system, especially the heart. For example, the ability to replace or repair diseased heart valves with prosthetic devices has provided surgeons with a method of treating heart valve deficiencies due to disease and congenital defects. A typical procedure involves removal of the native valve and surgical replacement with a mechanical or bioprosthetic valve. Another technique uses an annuloplasty ring to provide structural support to the natural annulus of the valve.

Prosthetic Valve Endocarditis (PVE) is an infection that can be associated with a heart valve prosthesis. Bacteria can form colonies at the surgical site associated with the implant and in the fabric of the sewing cuff of the valve prosthesis. The growth of tissue into the sewing cuff material also is associated with the attachment of bacteria and other pathogens. For this reason, heart valve recipients are cautioned regarding activities that may introduce bacteria into the bloodstream, such as dental work. For tissue replacement valves, PVE more commonly is associated with the leaflet portion of the valve rather than the sewing cuff portion of the valve.

PVE can be caused by gram-negative bacteria, gram-positive bacteria, fungi or rickettsia. PVE caused by gram-positive bacteria is particularly prevalent. Diagnosis is based generally on two positive blood cultures for the same organism along with clinical symptoms. Certain organisms are difficult to culture, however, which can complicate diagnosis.

With respect to replacement heart valves, care must be taken to ensure sterility during production and to prevent contamination during the replacement valve implantation process. For example, some tissue heart valves are stored in sterilizing solutions. In addition, to ensure sterility or to reduce perioperative contamination, some surgeons apply antibiotics to the prosthesis prior to implantation.

Articles used in in vitro and in vivo biological procedures may also require sterilization. Contamination of the articles used in biological procedures with undesirable microbes can result in erroneous results. Microbial contamination of culture flasks, for example, can lead to proliferation of microbes and inhibition of the desired cell cultures.

Analysis of biological samples, for example, can be conducted using optical methods such as absorption or transmittance of light. Assays using optical methods can determine the quantity of cells in a sample. The presence of contaminating microbes in a cell culture, however, can lead to erroneous data regarding the number of cells present in a sample. This can lead to experimental setbacks of days, months and sometimes even years, especially if the microbial contamination is not detected early.

SUMMARY OF THE INVENTION

In a first aspect, the invention pertains to a method of treating an article. The method includes contacting the article with a sterilizing composition. The sterilizing composition includes an epoxy amine compound and an alcohol.

In a further aspect, the invention pertains to a method of treating an article including cross-linked tissue. The method includes contacting the article with a sterilizing composition that includes an epoxy amine compound. The cross-linked tissue generally has been further processed prior to contact with sterilizing composition.

In another aspect, the invention pertains to a method of treating a non-proteinaceous article. The method includes contacting the article with a sterilizing composition that includes an epoxy amine compound.

In a further aspect, the invention pertains to a sterilizing composition including an epoxy amine compound and an alcohol.

DETAILED DESCRIPTION OF THE PREFERRED EMBODIMENTS

New approaches are described for treating articles, particularly biological and medical articles. These approaches include the use of epoxy amine compounds as antimicrobial agents. Sterilizing compositions that include epoxy amine compounds and, optionally, alcohol are described herein. In particular, the new method of treating articles includes contacting the articles with a sterilizing composition that includes one or more epoxy amine compounds.

Furthermore, proteinaceous articles that have been subject to cross-linking processes followed by additional techniques can also be treated using the sterilizing compositions. The articles can be treated for a limited period of time. Alternatively, the articles can be stored in contact with epoxy amine sterilizing compositions for long periods of time in order to maintain the sterility level of a sterilized article.

Sterilizing compositions as referred to herein are compositions that are toxic to some or all microorganisms and/or that are bacteriostatic such that they maintain the sterility of a sterile article.

Relevant articles include biocompatible medical articles and biological articles. Articles are biocompatible, in that they are non-toxic, non-carcinogenic and do not induce hemolysis or a significant immunological response. Biological articles, as referred to herein, relate to articles used in in vitro and in vivo biological procedures.

A variety of medical articles can be used to contact bodily fluids of a patient. Relevant medical articles generally incorporate a biocompatible material which is intended to contact the patients' biological fluids and/or tissues. Bodily fluids include, for example, blood, plasma, serum, interstitial fluids, saliva and urine. The patient can be an animal, especially a mammal, and preferably is a human. Medical articles include, for example, implantable medical devices, surgical instruments, dental instruments, catheters and the like. Contact of a medical article with a patient's bodily fluids may generate a risk of infection.

A variety of biological articles used in biological procedures may require a sterile environment. Relevant biological articles are generally sterilized prior to contact with fluids used in biological procedures. Fluids used in biological procedures include, for example, cell cultures, bacterial cultures, tissue cultures, culture media, saline solutions, buffers, and the like.

The articles that can be treated using the approaches described herein can include proteinaceous and/or non-proteinaceous articles. Proteinaceous as referred to herein relates to materials that include polypeptides that may be cross-linked. The proteinaceous articles may be cross-linked prior to treatment with the sterilizing composition. In some embodiments, the proteinaceous articles may be cross-linked and further processed, such as by attaching sewing cuffs or by treating with an anti-calcification agent, prior to treatment with the sterilizing composition.

The novel sterilizing compositions described herein include epoxy amine compounds, preferably polyepoxy amine compounds, as antimicrobial agents. Epoxy amine compounds are molecules that generally include both an amine moiety (e.g. a primary, secondary, tertiary, or quaternary amine moiety) and an epoxide moiety. Epoxy amine compounds include, for example, polyepoxy amines such as diepoxy amines, triepoxy amines and quaternaryepoxy amines. Furthermore, epoxy amine compounds can readily self-polymerize to form a distribution of oligomers of various sizes.

Epoxy amine compounds used in the sterilizing composition as described herein can include the monomeric form and/or the oligomeric forms of the epoxy amine compound. In a preferred embodiment, sterilizing compositions include triglycidyl amine. The sterilizing composition can also include a distribution of triglycidyl amine oligomers that form as a result of self-polymerization. The sterilizing composition may include more than one type of epoxy amine compound.

The sterilizing compositions preferably include alcohol in addition to the epoxy amines. The sterilizing composition may also include additional antimicrobial agents. In some embodiments, the sterilizing compositions may also include surfactants.

The methods described herein include contacting the articles with the sterilizing composition. The contact may include, for example, immersing the article in the composition, coating a surface of the article with the sterilizing composition, exposing the article to vapors of the sterilizing composition and the like.

Epoxy amine compounds may act as a bactericidal and/or a bacteriostatic agent. Bactericidal agents inactivate the viable microbes whereas bacteriostatic agents inhibit proliferation of viable microbes, i.e. prevent replication but not necessarily the metabolism of the microbes. Epoxy amine compounds can be effective against microbes such as bacteria, fungi, protozoa, yeast and the like. Sterilizing compositions that include epoxy amine compounds can be used to sterilize and store the articles described herein.

In some embodiments, contact with the sterilizing composition can inactivate the viable microbes associated with the articles. Contact with the sterilizing composition preferably results in a sterilized article.

In other embodiments, contact with the sterilizing composition can substantially inhibit proliferation of microbes, thus maintaining the level of microbes associated with the articles. In these embodiments, the epoxy amine compounds in the sterilizing compositions act as bacteriostatic agents. Treatment of sterile articles with the sterilizing composition, preferably, maintains the sterility of the article.

The invention also includes articles that are stored in the sterilizing compositions described herein. Articles may be sterilized and also stored in the epoxy amine sterilizing composition. Alternatively, the articles may be sterilized using other known techniques and subsequently stored in sterilizing compositions that include epoxy amine compounds. In some embodiments, the articles are stored in compositions that include epoxy amine compounds and alcohol.

A. Articles

Articles that can be treated using the approaches described herein include biological and medical articles. Relevant medical articles include all articles that contact bodily fluids and/or tissues. Medical articles can include devices organized generally into three groups: implanted devices, percutaneous devices and cutaneous devices. Implanted devices broadly include articles that are fully implanted in a patient, i.e., are completely internal. Percutaneous devices include items that penetrate the skin, thereby extending from outside the body into the body. Cutaneous devices are used superficially, for example, at a wound site or at a moist membrane.

Implanted devices and components thereof also include, without limitation, prostheses such as pacemakers, electrical leads such as pacing leads, defibrillators, artificial organs such as artificial hearts, ventricular assist devices, anatomical reconstruction prostheses such as jaw implants, heart valves, heart valve stents, valve leaflets, orifice rings of mechanical heart valves, pericardial patches, surgical patches, structural stents, vascular shunts, biological conduits, pledgets, suture, annuloplasty rings, staples, connectors, dermal grafts for wound healing, orthopedic and spinal implants, orthopedic pins, intrauterine devices (IUDs), urinary stents, permanently indwelling pericardial devices, maxial facial reconstruction plating, dental implants, intraocular lenses, clips, sternal wires, bone prostheses, skin prostheses, ligament prostheses, tendon prostheses, and combinations thereof.

Implantable devices of particular interest include implantable vascular devices. "Vascular" sites and structures as used herein include cardiovascular sites and structures and other blood contacting sites and structures. Implantable vascular devices include, for example, vascular stents, vascular grafts and conduits, valved grafts, coronary stents, heart valves and patches.

Percutaneous devices include without limitation angioplasty balloons, catheters of various types, cannulas, drainage tubes such as chest tubes, surgical instruments such as forceps, retractors, needles, gloves and catheter cuffs. Catheters can be used for accessing various bodily systems such as the vascular system, the gastrointestinal tract, or the urinary system.

Cutaneous devices include, without limitation, skin grafts, burn dressings, wound dressings of all types, dental hardware such as bridge supports and bracing components and contact lenses. Medical articles can also include instruments such as surgical instruments, dental instruments and the like.

Relevant biological articles include articles that contact fluids used in biological procedures. Biological articles can include, for example, flasks, tubes, tissue culture plates, microtiter plates, cell culture flasks, bioreactors and the like. Biological articles can also include articles that dispense fluids used in biological procedures, for example, pipetmen, pumps, other aliquoting mechanisms and the like. Biological articles can also include devices that are used to store fluids used in biological procedures.

B. Materials

Medical articles and biological articles made from varying materials can be successfully treated with the sterilizing compositions of the invention. The medical articles described above are generally made from biocompatible materials including natural materials, synthetic materials or combinations thereof. The materials can be proteinaceous materials and/or non-proteinaceous materials. Proteinaceous materials can include other non-peptide components, such as carbohydrates, lipids, nucleic acids and/or other natural or synthetic compounds, which may or may not be covalently bonded to the polypeptide.

Natural material for use in the invention includes relatively intact (cellular) tissue, decellularized and recellularized tissue. These tissues may be obtained from, for example, native heart valves; portions of native heart valves such as roots, walls and leaflets; pericardial tissues such as pericardial patches; connective tissues; bypass grafts; tendons; ligaments; skin patches; blood vessels; cartilage; dura matter; skin; bone; fascia, submucosa and umbilical tissues; and the like.

Natural tissues are derived from a particular animal species, typically mammalian, such as human, bovine, porcine, seal or kangaroo. These natural tissues generally include collagen-containing material. Natural tissue is typically, but not necessarily, soft tissue. Appropriate tissues also include tissue equivalents such as tissue-engineered material involving a cell-repopulated matrix, which can be formed from a polymer or from a decellularized natural tissue.

Biocompatible tissues can be fixed by cross-linking the amino acids present in the tissues. This provides stabilization, for example, by preventing enzymatic degradation of the tissue. Glutaraldehyde is typically used for fixation, but other fixatives can be used, such as epoxy amines, epoxides, other difunctional aldehydes, carbodiimide, genipin and formaldehyde. Biocompatible materials can be used in either cross-linked or uncross-linked form, depending on the type of tissue, the use and other factors. Cross-linked materials may also be contacted with the sterilizing compositions. Cross-linked materials that have been further processed, such as treatment with anticalcification agents and/or attachment of sewing cuffs, may also be contacted with the sterilizing compositions. Cross-linked materials, for example, treated with anticalcification agents, such as aluminum chloride ($AlCl_3$), may be contacted with the sterilizing compositions.

Relevant synthetic materials include, for example, polymers, metals and ceramics. Appropriate ceramics include, without limitation, hydroxyapatite, alumina and pyrolytic carbon. Suitable metals include, for example, titanium, stainless steel, cobalt, and alloys such as Elgiloy®, a cobalt-chromium-nickel alloy and Nitinol®, a nickel-titanium alloy. Polymeric materials can be fabricated from synthetic polymers as well as purified biological polymers. Appropriate synthetic materials include hydrogels and other synthetic materials that cannot withstand severe dehydration.

Appropriate synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, polydimethyl siloxanes, cellulose acetates, polymethyl methacrylates, ethylene vinyl acetates, polysulfones, nitrocelluloses and similar copolymers. These synthetic polymeric materials can be woven into a mesh to form a matrix or substrate. Alternatively, the synthetic polymer materials can be, for example, molded or cast into appropriate forms.

Biocompatible polymers can be naturally occurring or produced in vitro by, for example, fermentation and the like. Purified biological polymers can be appropriately formed into fibers or yarn and then into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch), nucleic acids and copolymers thereof.

Biocompatible materials can include a combination of the various natural materials and synthetic materials described above. The biocompatible materials also can include metal portions. Some relevant prosthetic materials are made completely from metal, ceramics or a combination of metal, ceramics and, optionally, additional natural or synthetic materials. Mechanical heart valves are relevant products, which generally are made from metallic, polymeric and/or ceramic components. The medical articles can also be made from any of the suitable materials described below for biological articles.

The biological articles described herein can be made from any one or a combination of the materials described above for medical articles. Other suitable materials for biological articles can include, for example, glass such as pyrex, metal, polycarbonate, polyproponate, polystyrene and the like.

Suitable materials for biological articles can also include materials that are non-biocompatible.

C. Sterilizing Compositions

The sterilizing compositions described herein include one or more epoxy amine compounds. Epoxy amines are molecules that generally include both an amine moiety (e.g. a primary, secondary, tertiary, or quaternary amine) and an epoxide moiety. The epoxy amine compound in the sterilizing compositions can be a monoepoxy amine compound and/or a polyepoxy amine compound. The epoxy amine compound is preferably a polyepoxy amine compound having at least two epoxide moieties and possibly three or more epoxide moieties. In more preferred embodiments, the polyepoxy amine compound is TGA.

Figure 1:
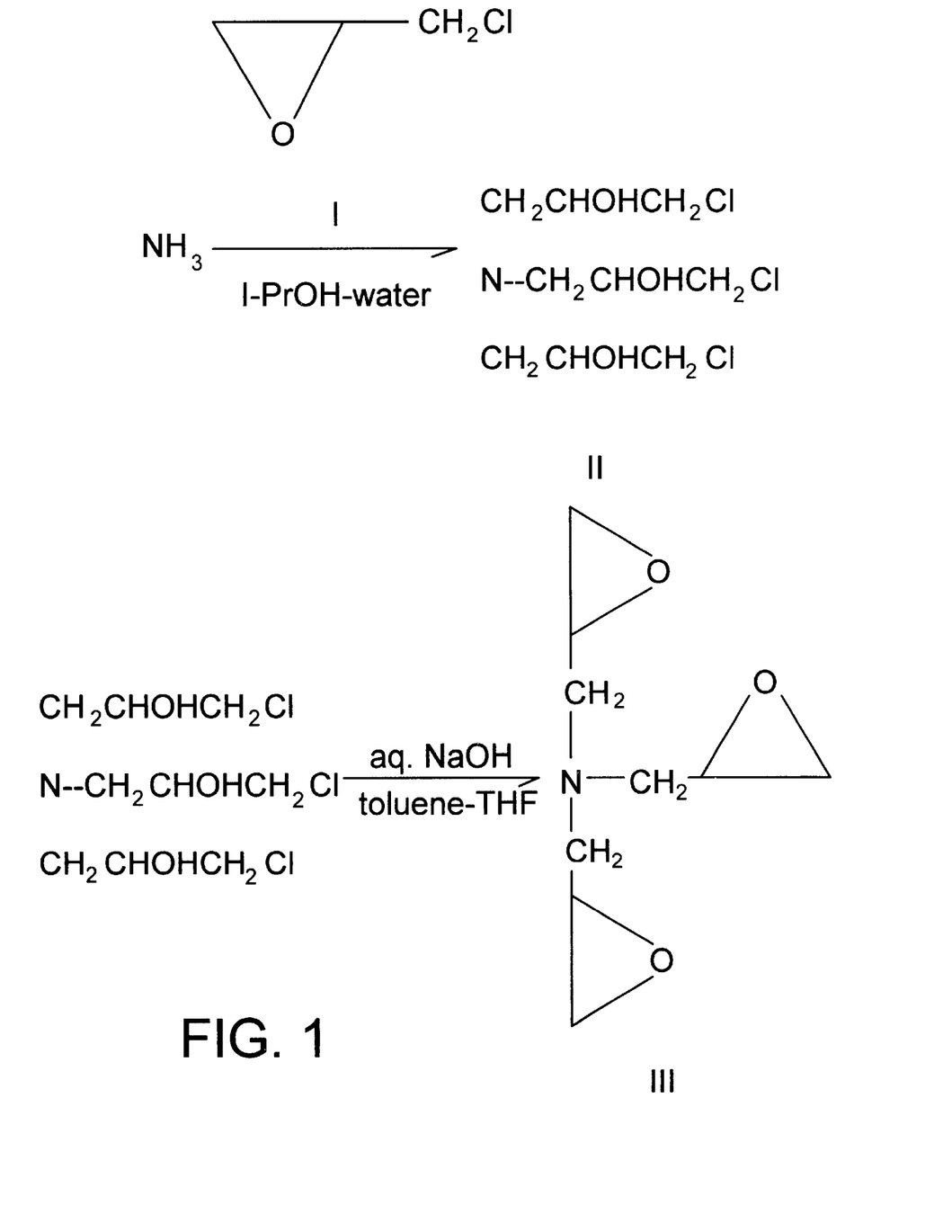
FIG. 1 is a schematic of a synthetic method for preparing triglycidyl amine (TGA).

In preferred embodiments, the epoxide ring is separated from the nearest amino moiety by between 1 and 5 atoms, a $C_1$–$C_5$ branched or linear alkyl or substituted alkyl chain, such as the methylene group, which separates the epoxide ring and the tertiary amine moiety in TGA as seen in FIG. 1. Other chemical groups which can be interposed between the epoxide ring and the nearest amino moiety include, for example, branched or linear alkenyl chains, substituted alkyl chains, ring groups and aromatic groups.

Polyepoxy amine compounds can be synthesized using methods known in the art. These methods include, for example, a modification of approaches described by Ross et al., 1963 J. Org. Chem. 29:824–826, Martyanova et al., 1990, Sb. Nauch. Tr. Lenengr. In-t Kinoinzh. 2:139–141 (Chem. Abst. Nos. 116:43416 and 116:31137) and Chezlov et al., 1990, Zh. Prikl. Khim. (Leningrad) 63:1877–1878 (Chem. Abst. No. 114:121880), all of which are incorporated herein by reference.

A method of synthesizing TGA is depicted in FIG. 1. Briefly, epichlorohydrin (compound I in FIG. 1) is combined with ammonia and isopropanol. The mixture ultimately yields a viscous syrup. The syrup after further incubation, can be dissolved in toluene and concentrated under reduced pressure to yield tris-(3-chloro-2-hydroxypropyl) amine (compound II in FIG. 1). Compound II can be dissolved in toluene, followed by addition of tetrahydrofuran, sodium hydroxide and water. The organic layer can be separated from the aqueous layer and dried overnight with a dessicant. After removing the dessicant, the solution can be concentrated under reduced pressure and the residue distilled to yield TGA (Compound III in FIG. 1). TGA can be recovered as a viscous liquid, having a boiling point of 98° C.–101° C. Liquid TGA can solidify upon refrigeration and remain a solid when returned to room temperature.

Figure 2:
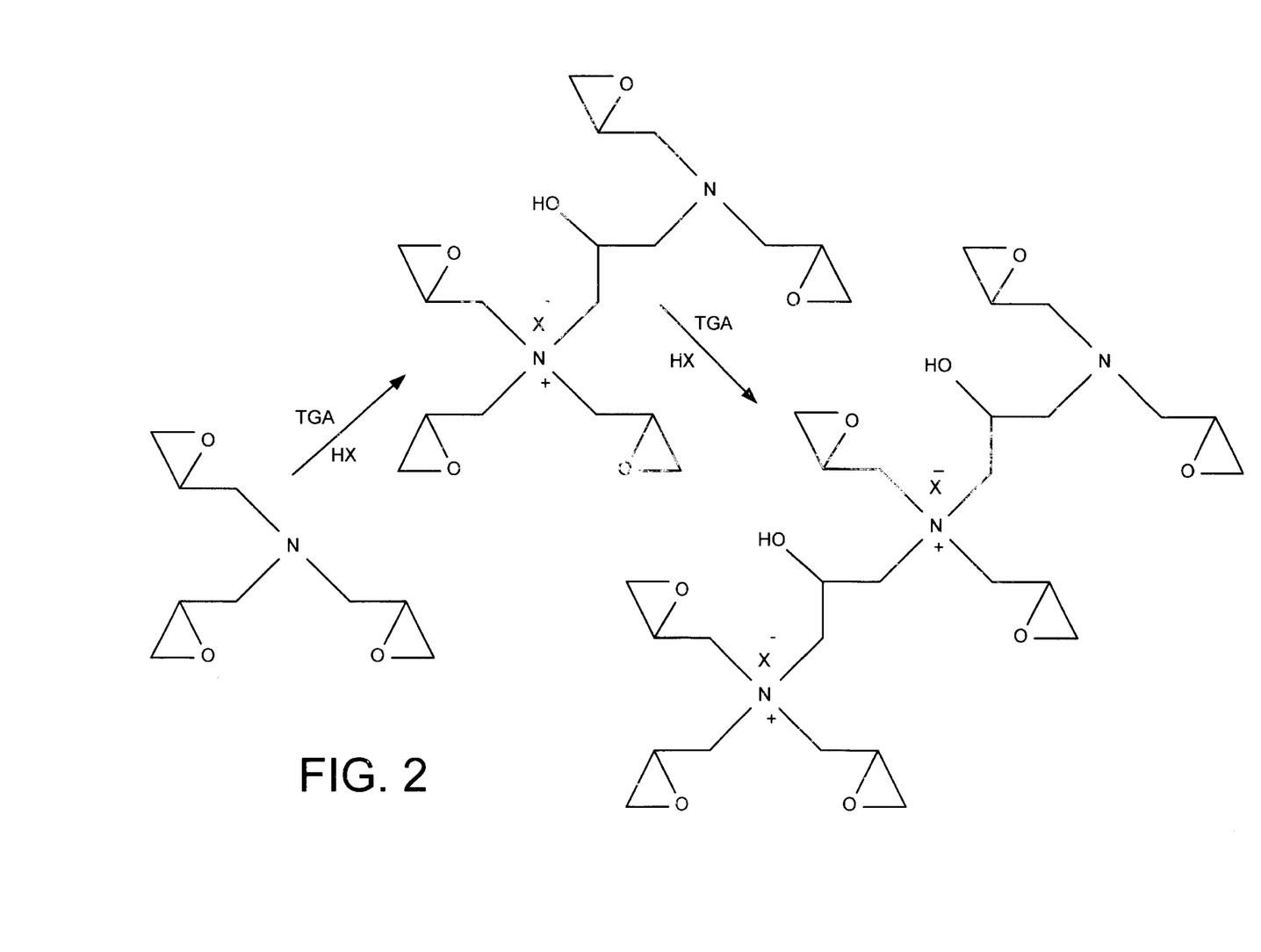
FIG. 2 is a diagram of formation of some TGA oligomers.

Polymerization of the polyepoxy amine compounds can also result in additional forms of polyepoxy amine compounds. It is recognized that a polymer formed by polymerizing polyepoxy amine compounds (e.g. TGA, as shown in FIG. 2) can be used in sterilizing compositions. The polymers generally are formed by self-polymerization of polyepoxy amine compound molecules if left for a period of time. Self-polymerization occurs when epoxy moieties react with the primary, secondary or tertiary amines. Polymerization of a polyepoxy amine compound can lead to formation of a polymer having a plurality of quaternary ammonium moieties. When an epoxy amine polymer is used, the polymer can be a linear polymer or a branched polymer, and preferably has a molecular weight of about 185 to 10,000. For example, a polymer of TGA can be used in which the polymer is formed by polymerization of at least about 15 TGA molecules, yielding a TGA polymer having a molecular weight greater than 3000. Sterilizing compositions, thus, can include monomers of the polyepoxy amine compound and/or a distribution of oligomers of the polyepoxy amine compound due to the self-polymerization.

In some embodiments, only one epoxy amine compound is used in the sterilizing compositions. In other embodiments, a plurality of epoxy amine compounds are used in the sterilizing compositions, such as a combination of TGA and a quaternary form of epoxy amine.

The epoxy amine compounds are more readily soluble, due to their smaller size, than standard epoxy compounds, which is particularly advantageous for use in the sterilizing compositions described herein. The epoxy amine compounds can be readily solubilized without the aid of surfactants. The epoxy amine compounds also have higher reactivity than other epoxy compounds. Without being bound to any particular theory, it is thought that the higher reactivity can lead to reduced cytotoxicity. The sensitivity of microbes to epoxy amine compounds coupled with reduced cytotoxicity to eukaryotic cells makes epoxy amine compounds particularly advantageous for use as antimicrobial agents for medical devices.

Suitable concentrations of the epoxy amine compounds in the sterilizing composition can be selected. Generally, the concentration of the epoxy amine compounds is sufficient to sterilize the articles to a desired level. The suitable concentration of the epoxy amine compounds in the sterilizing composition can vary depending, for example, on the article to be sterilized, the intended use of the article, the expected microbial load prior to sterilization, the material of the article, the length of desired contact with the sterilizing composition, the particular epoxy amine compound used and the like.

To reduce the risk of subsequent contamination of the article, the sterilized articles can be stored in contact with a bacteriostatic agent. The articles may, however, be used shortly or immediately following the sterilizing procedure. It may be desirable to limit the quantity and/or concentration of the epoxy amine compounds and any other components of the sterilizing compositions to reduce the risk of cytotoxicity. Inappropriately high concentration of the epoxy amine compounds can result in tissue degeneration, cellular lysis, physical degradation of the article and the like. In some embodiments, the articles may be contacted with high concentrations of the epoxy amines in the sterilizing compositions but may be rinsed to reduce and/or eliminate the amount of sterilizing composition present on or within the article.

For most embodiments, the concentration of the epoxy amines in the sterilizing composition can vary between about 0.5 percent by weight to about 10 percent by weight, preferably between about 3 percent by weight to about 8 percent by weight, and more preferably between about 6 and about 7 percent by weight.

Generally, the epoxy amine compounds are solubilized, preferably in water, for use as a sterilizing composition. The sterilizing composition with the epoxy amine compounds solubilized in water can be used to contact the articles described herein. Alternatively, the sterilizing composition can be vaporized. The vaporized sterilizing composition is directed at the desired articles for contact. The vaporized sterilizing composition may include only epoxy amine compounds. Alternatively, the vaporized sterilizing composition can include additional components, for example, alcohol. The sterilizing composition may be vaporized by heating, or by using an atomizing apparatus, for example, a sprayer, or a combination thereof.

The sterilizing compositions may also include alcohol. If alcohol is present in the sterilizing compositions, the concentration of the alcohol is generally between about 5 percent by weight and about 50 percent by weight, preferably between about 5 percent by weight and about 30 percent by weight and more preferably between about 10 percent by weight and about 20 percent by weight.

Suitable alcohols include aliphatic and aromatic alcohols. Suitable aliphatic alcohols include methanol, ethanol, n-propanol, isopropanol, n-butanol, isobutanol, sec-butanol, t-butanol, cyclohexanol, n-octanol, allyl alcohol, and the like. Suitable biocompatible aromatic alcohols include benzyl alcohol, cresol, carbinol, and the like. These alcohols are used to solubilize the waxy, polysaccharide coating of bacteria and are generally mildly effective by themselves in destroying microorganisms and thus create synergy with and enhance the antimicrobial capacity of the epoxy amine compositions.

The sterilizing compositions may include other antimicrobial agents in addition to the epoxy amines. A wide variety of other antimicrobial agents are known. Suitable antimicrobial agents that can be used in conjunction with the epoxy amine compounds in the sterilizing compositions may include toxins. Suitable toxins may have specificity for microorganisms, i.e. prokaryotes, yeasts or Protista, to promote preferential destruction of microorganisms over cells of a patient. Some preferred toxins also have specific effectiveness against particular types of microorganisms, such as a particular species of bacteria. For example, proton pump inhibitors, such as omeprazole and lansoprazole, are bacteriocidal against *Helicobacter pylori*. See Figura et al., "In vitro activity of lansoprazole and *Helicobacter pylori*," J. Antimicrobial Chemotherapy, 39:585–590 (1997), incorporated herein by reference.

Suitable antimicrobial agents also include traditional antibiotics. Some antibiotics are polypeptiedes, such as actinomycin, bacitracin, circulin, fungisporin, gramicidin S, malformin, mycobacilin, polymyxin, tyrocidine and valinomycin.

Generally, specific antibiotics block cellular activity specific for microbial function. For example, several antibiotics, such as penicillin, phosphonomycin, bacitracin and vancomycin, interfere with cell wall synthesis. In particular, penicillin inhibits a cross-linking reaction in cell wall synthesis. Other antibiotics, such as streptomycin, tetracycline chloramphenicol and erythromycin, act by inhibiting protein synthesis by binding to bacterial ribosomes. In some embodiments, a solution of ampicillin (1 gram/liter) may be used.

The sterilizing compositions may also include surfactants. Generally, from about 1 to about 40 percent by weight and preferably from about 5 to about 20 percent by weight of surfactant is added to an aqueous solution if a surfactant is used.

Suitable organic surfactants include anionic, cationic, and nonionic surfactants and their salts. The preferred salts of the surfactants in the present invention include sodium and potassium. Anionic surfactants useful in the present invention are those having a relatively large hydrophobic region of hydrocarbon residues, including aliphatic and aromatic groups, bonded to a negatively charged ionic group. The aliphatic residues may be branch chained, straight chained, cyclic, heterocyclic, saturated or unsaturated. These hydrophobic residues can be connected directly to an anionic group, such as carboxylate, sulfate, or sulfonate groups; or can be connected thereto through an intermediate linkage, such as an ester, amide, sulfonamide, ether, or aryl group. Anionic surfactants in one embodiment of the present invention are those having one or more carboxylates bonded to an alkyl side chain, to a steroid, or to amino acids in the side chain, such as in the bile acids.

Other components may be included in the sterilizing compositions to obtain desired properties. Buffering systems may be included in order to maintain the sterilizing composition in a desired pH range. Suitable buffers can be based on, for example, the following compounds: ammonium, phosphate, borate, bicarbonate, carbonate, cacodylate, citrate, and other organic buffers such as tris (hydroxymethyl) aminomethane (TRIS), morpholine propanesulphonic acid (MOPS), and N-(2-hydroxyethyl) peperazine-N'-(2-ethanesulfonic acid) (HEPES). Suitable buffers are generally chosen based on the desired pH range for the sterilizing composition. TRIS buffers, for example, act as buffers in the pH range of between about 6 and about 8.

The desirable pH range for the sterilizing compositions can vary depending on the nature of the article to be sterilized. Articles that include tissue, for example, can be sensitive to the pH of the environment and thus, generally are sterilized using sterilizing compositions at a pH within the physiological range. Articles that include only metal, for example, may be sterilized at a pH outside of the physiological pH range (pH 6–8). Generally, the activity of the epoxy amine compound increases with increasing pH. Epoxy amine compounds can have high activity even at a pH greater than about 9.

Salts and/or saline solutions may be included in the sterilizing compositions to provide appropriate electrolyte balance. Suitable salts include, for example, sodium salts, potassium salts, phosphates and the like.

Generally, articles that include tissue are sterilized using sterilizing compositions and conditions near physiological ranges. Thus, the temperature, pH, electrolyte balance and the like are all generally near the physiological ranges for articles that include tissue. The physiological ranges compatible for tissue are documented in the art.

D. Methods of Sterilization

The sterilization approaches described herein include contacting the article with a sterilizing composition that includes one or more epoxy amine compounds as antimicrobial agents. The article may be contacted with the sterilizing composition in a variety of ways including coating the sterilizing composition on or into the article, immersing the article in the sterilizing composition, exposing the article to vapors of the sterilizing composition and the like. All or a portion of the article may be contacted with the sterilizing composition. The contact may include the exterior of the article, the interior of the article or both.

The articles preferably are contacted with the sterilizing composition until the articles are substantially sterile. The measurement standard used by the medical industry for evaluating the effectiveness of a sterilization procedure is known as the Sterility Assurance Level (SAL). The level of SAL acceptable by the medical industry is 6, which represents the probability that a surviving target organism remains after the lapse of a specified time period is less than $1 \times 10^{-6}$. The SAL value is calculated as the negative base 10 logarithm of the microbial survivor probability. The amount of time necessary to achieve the acceptable sterility for a particular procedure as used on a specific target organism is calculated from a measured unit of time known as the D-value.

The D-value generally represents the amount of time in minutes necessary to reduce a population by 90% (one log unit) in the count level of viable target organisms after the application of the sterilization procedure, with a lower D-value time representing a more efficient procedure. The D-value can depend upon the conditions under which the procedure is performed, such as the temperature, the specific sterilant being used and the concentration of the sterilant in the sterilizing composition.

Minimum effective sterilization time relates to the minimum amount of time the articles have to be exposed to the sterilizing compositions to be effectively sterile. For medical articles, the minimum effective sterilization time is the amount of time required to reach the SAL value of 6. For non-medical articles, an SAL value of 6 may be desirable in some embodiments. In other embodiments, a SAL value of 1 may be sufficient, in which case, the minimum effective sterilization time may only be the D-value time, i.e. the time to reach a 90% reduction in microbial load. Articles may be contacted with the sterilizing composition for only the minimum effective sterilization time. Alternatively, articles may be contacted with the sterilizing composition for longer periods of time than the minimum effective sterilization time.

As discussed above, the D-value can depend on the temperature at which the sterilization is conducted, referred to herein as the sterilization temperature. Generally, as the sterilization temperature increases, the D-value time decreases. Conversely, as the sterilization temperature decreases, the D-value time increases. In some embodiments, sterilization temperature may be increased to attain lower D-values.

Similarly, as the concentration of the sterilant in the sterilizing composition increases, the D-value of the antimicrobial procedure decreases. In some embodiments, it may be preferable to have a low D-value for the sterilizing procedure, and thus, higher concentrations of the sterilant may be used. In other embodiments, it may be preferable to use low concentrations of the sterilant, and thus the sterilization procedure may have a high D-value.

With epoxy amine compounds used as antimicrobial agents, the D-value is generally at least about 30 minutes. The D-value can be between about 1 hour and about 48 hours. In some embodiments, the D-value is between about 3 hours and about 12 hours. The sterilant, the concentration of the sterilant and the sterilization temperature can be selected based on the desired time of sterilization.

Preferred sterilization times generally also depend on the use of the article. In some embodiments, longer sterilization times may be preferred, for example, when the article is being stored in the sterilizing composition until it is used. In other embodiments, however, it may be preferable to only sterilize for the minimum effective sterilization time.

The sterilization temperature can vary depending on the type of article to be sterilized, the desired time of sterilization, the concentration of the epoxy amine compound in the sterilizing composition and the like. Heat sensitive articles may be sterilized at temperatures that are not deleterious to the article. The sterilization temperature may be less crucial to heat insensitive articles. Surgical instruments, for example, may be sterilized at very high temperatures but articles with tissue are generally sterilized at lower temperature in order to maintain integrity of the tissue.

The stability of the components present in the sterilizing composition can determine the appropriate sterilization conditions. TGA, for example is generally stable in the freezer for about one year. Heating of TGA, however, results in self-polymerization. The sterilization temperature, for example, may depend on the epoxy amine compounds used in the sterilizing composition. Generally, the reactivity of the epoxy amine compound increases as the temperature increases. The sterilization temperature may also depend on any of the other components included in the sterilizing composition.

The sterilization temperature for heat sensitive articles, for example, articles that contain tissue, is preferably between about 10° C. and about 40° C., more preferably the sterilization temperature is between about 20° C. and about 30° C. The sterilization of other articles is dependent on the material properties of the article and generally can range between about 10° C. and 150° C.

The methods described herein may also be used to treat articles that include cross-linked tissue. Cross-linking of tissues can provide mechanical stabilization, for example, by preventing enzymatic degradation of the tissue. Glutaraldehyde is typically used for fixation, but other fixatives can be used, such as carbodiimides, epoxy amines, epoxides, formaldehyde and other difunctional aldehydes. After cross-linking, additional procedures may be performed in order to prepare the article for subsequent uses. These procedures include, for example, placement of sewing or bioresorbable cuffs on the articles, treatment with anti-calcification agents, growth factors and the like. The articles, after the post cross-linking procedures, can be treated using the sterilizing compositions and methods described herein.

The sterilizing compositions described herein may inactivate the microbes present on or within an article, e.g., the epoxy amine compound acts as a bactericidal agent. In some embodiments, the articles initially contain a substantial number of microbes. It is desirable in such cases to reduce the microbial load associated with the articles prior to contact with the bodily fluids and/or other fluids used in biological procedures. The articles thus can be treated with the sterilizing composition to reduce the microbial load to obtain sterile articles as described above.

In other embodiments, articles can be treated with the sterilizing compositions to inhibit proliferation of microbes, e.g., the epoxy amine compound acts as a bacteriostatic agent. The standard of measurement for a bacteriostatic agent is described by Block, S. S., in Disinfection, Sterilization and Preservation, p. 1050, Lea & Febiger, 1991. Suitable epoxy amine compounds can inhibit growth, for at least 7 days, when up to 100 viable microorganisms are associated with the article. Articles that have been sterilized using the methods described herein or using other methods known in the art, for example, ultraviolet radiation, heat, heat and pressure, and other chemical sterilants, can be stored in the sterilizing compositions described herein. Storage of the articles in the sterilizing compositions can maintain the sterility of the articles over long periods of time. Articles can generally be stored in the sterilizing composition for more than 1 day, alternatively for more than 30 days and in some embodiments, for more than 6 months. Articles that have not been sterilized may also be stored in the sterilizing compositions.

Articles can be stored in the sterilizing compositions described herein and packaged in containers, preferably sealed. The articles may be placed in a container with the appropriate amount of the sterilizing composition and then sealed. In some embodiments, the article is immersed in the sterilizing composition in the sealed container. In other embodiments, only a portion of the article may be in contact with the sterilizing composition in the container. Alternatively, the article may be stored in the presence of the sterilizing composition vapors. The sealed container may then be stored and/or distributed as desired for future use. The articles may have been sterilized prior to storage in the epoxy amine compositions.

E. Storage, Distribution and Use

The sterilizing compositions described herein can be used as sterilants, as storing agents and the like. The epoxy amine compounds alone can be stored and distributed as a solid, a paste, in solution, and/or in a vaporizable form. Alternatively, sterilizing compositions containing the epoxy amine compounds and any other optional components, preferably in solution, can be appropriately packaged, stored and/or distributed. In other embodiments, all the components of the sterilizing composition can be stored separately but packaged together for distribution. Prior to use, the components can be combined and/or solubilized to form the sterilizing compositions. The sterilizing composition can then be used to contact the articles for use as a sterilant and/or as a bacteriostatic agent. The packaging of any of the compositions described above are preferably in sealed containers.

The sterilizing composition can also be appropriately contacted with an article and stored. The stored article can be packaged and distributed as desired. The stored article may be packaged dependent on the nature of the article. Articles, in contact with the sterilizing composition, may be stored in refrigerators, freezers, room temperature, incubators and the like. Tissue, for example, may be placed in the sterilizing composition and stored at refrigeration and/or room temperatures. Medical articles such as heart valve bioprostheses, stored in the sterilizing compositions, generally are distributed in sealed containers to health care professionals. Generally, the articles are packaged with appropriate instruction labels.

The medical articles preferably are removed from the storage containers immediately before use. The article may be removed from the container and directly used. Alternatively, the article may be removed from the container and rinsed prior to use. The rinsing, preferably, is performed with a sterile composition.

EXAMPLES

Example 1-Sterilizing Compositions with Triglycidyl amine

This example relates to the effect of triglycidyl amine (TGA) on cultures of Bacillus subtilis (B.subtilis) in test tubes.

A suspension of B.subtilis at concentration of $2.5 \times 10^7$ colony forming units (CFU)/milliliter (ml) was prepared and mixed vigorously. TGA was synthesized according to the method shown in FIG. 1. A sterilizing composition of 0.2 M TGA (about 3.7% by weight) was prepared in HEPES buffer, at a pH of 7.2. The HEPES was obtained from Sigma Chemical Co., St. Louis, Mo. The TGA solution was then filter sterilized (solution #1). A volume of 50 mls of solution #1 and a volume of 0.1 ml of the B. subtilis suspension were added to a sterile test jar.

Negative control test jars contained equivalent volumes of sterile sterilizing composition without any added B. subtilis culture. Positive control test jars contained an equivalent volume of sterile Baxter™ irrigation saline (Lot#G946566) and an equivalent volume of B. subtilis suspension in the test jar.

A sterile magnetic bar was placed in each test jar, and the jars were placed in a stirring water bath. The temperature of the water bath was maintained at 24° C.

An aliquot of 1 ml was removed from each test jar, in triplicate, at time points of 0.5 hours, 2 hours, 4 hours, 6 hours, 22 hours, 24 hours, 26 hours, 28 hours and 30 hours.

The 1 ml aliquots were removed from the test jar, diluted, if necessary, to achieve countable microbial populations and filtered through separate sterile membrane filters. Each membrane filter was then vacuum rinsed using a 100 ml aliquot of sterile USP fluid A (Lot 100581UK) obtained from Difco, Detroit, Mich., to remove residual sterilizing composition. USP fluid A is a 1 gram per 100 milliliter solution of peptamin. The Fluid A was allowed to sit for one minute prior to drawing the vacuum. One rinse with the Fluid A was conducted with each aliquot. Each of the aliquots were treated in the same manner.

After rinsing, each membrane filter was placed on the surface of tryptic soy agar plates and incubated at between about 30° C. and about 35° C. for a minimum of about 3 days. Upon completion of the incubation period, the colonies present on all plates were counted visually.

Figure 3:
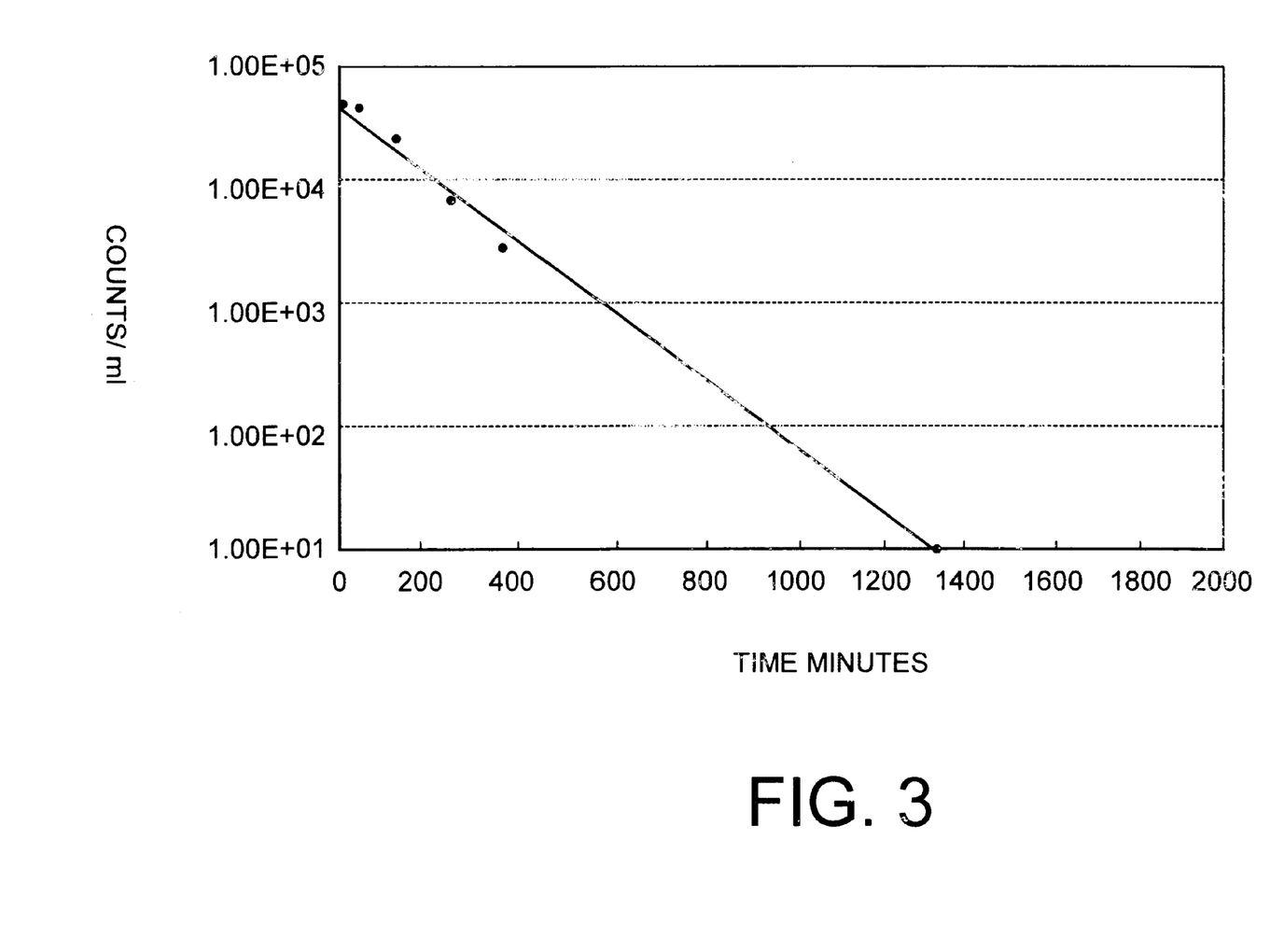
FIG. 3 is a plot of the average $\log_{10}$ count of *B.subtilis* colonies versus time of incubation with the polyepoxy amine sterilizing composition of solution 1.
Figure 4:
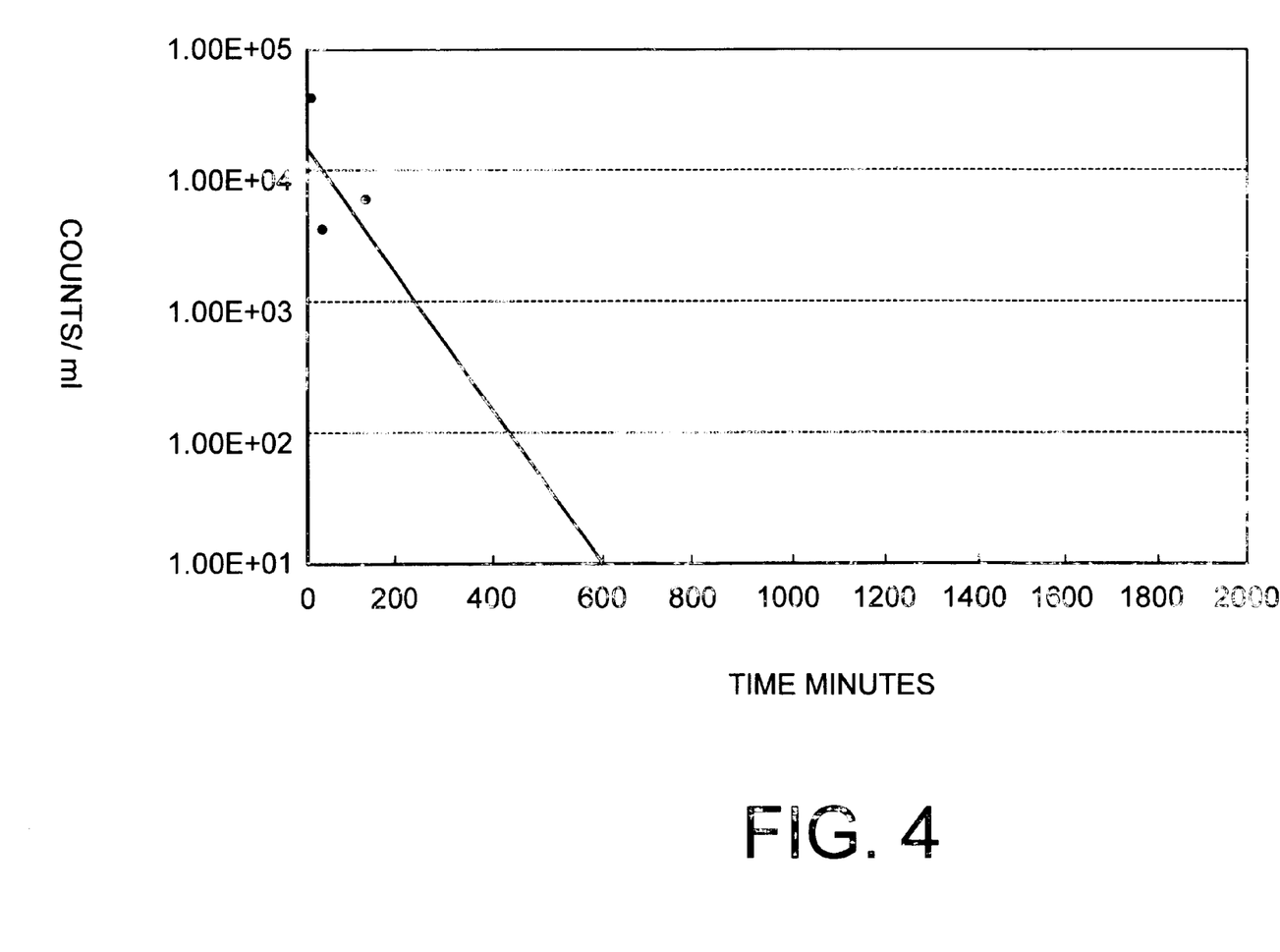
FIG. 4 is a plot of the average $\log_{10}$ count of *B.subtilis* colonies versus time of incubation with the polyepoxy amine sterilizing composition of solution 2.

The D-value for the sterilizing composition was calculated. In order to calculate the D-value, a triplicate average colony count was determined and the log (base 10) of the average for each time interval was recorded. The log average was plotted as a function of time as seen in FIGS. 3 and 4. A linear regression analysis of the data was performed to determine the slope of the plot in FIG. 3 and 4. The D-value of the sterilizing composition was defined as the slope of the curves of the plots shown in FIG. 3 and 4.

As calculated from the data plotted in FIG. 3, the sterilizing composition containing 0.2 M of TGA (Solution #1) had a D-value of 357.1 minutes at 24° C. (for a 24 hour sterilization period). The negative control did not have any colonies and the positive control had microbial growth expected from cultures without any sterilizing composition.

Example 2-TGA and Ethanol Sterilizing Compositions

This experiment relates to evaluating the antimicrobial effectiveness of a sterilizing composition that includes ethanol as well as TGA. The experiments were conducted as described above in Example 1 except that a sterilizing composition was prepared that contained about 0.2 M TGA (about 3.7% by weight) and about 20% ethanol by weight (solution #2).

The results from the experiment are shown in FIG. 4 for this sterilizing composition (solution #2). As calculated from the data plotted in FIG. 4, the D-value for solution #2 at 24° C. from a 24 hour sterilization period is about 125.0 minutes. Thus, a combination of alcohol and TGA provides for extremely good sterilization properties. The negative and positive results were as described in Example 1. The effects of ethanol alone are known in the art. Briefly, ethanol at a concentration of about 70 percent by weight is only mildly bactericidal. Ethanol is known to be more of a bacteriostatic agent than a bactericidal agent. Thus, the combination of alcohol and epoxy amine was synergistic with respect to antimicrobial effectiveness.

The embodiments described above are intended to be illustrative and not limiting. Additional embodiments are within the claims. Although the present invention has been described with reference to preferred embodiments, workers skilled in the art will recognize that changes may be made in form and detail without departing from the spirit and scope of the invention.

What is claimed is:

1. A method of treating an article, the method comprising contacting the article with a sterilizing composition comprising an epoxy amine compound and an alcohol.

2. The method of claim 1, wherein the contact inactivates microbes associated with the article.

3. The method of claim 1, wherein the contact reduces the viable microbes associated with the article by about $1 \times 10^{-6}$.

4. The method of claim 1, wherein the contact inhibits microbial proliferation.

5. The method of claim 1, wherein the epoxy amine compound is a polyepoxy amine.

6. The method of claim 1, wherein the epoxy amine compound is triglycidyl amine.

7. The method of claim 1, wherein the articles are medical articles.

8. The method of claim 1, wherein the articles comprise tissue.

9. The method of claim 1, wherein the articles are biological articles.

10. The method of claim 1, wherein the composition comprises the epoxy amine compound at a concentration between about 0.5 percent by weight to about 10 percent by weight.

11. The method of claim 1, wherein the composition comprises the epoxy amine compound at a concentration between about 3 percent by weight to about 8 percent by weight.

12. The method of claim 1, wherein the article is contacted with the composition between about 1 hour and about 48 hours.

13. The method of claim 1, wherein the article is contacted with the composition for greater than about 48 hours.

14. The method of claim 1, wherein the article is contacted with the composition at a temperature between about 10° C. and about 40° C.

15. The method of claim 1, wherein the composition is an aqueous solution.

16. The method of claim 1, wherein the composition is vaporized.

17. The method of claim 1, wherein the contact comprises immersing the article in the sterilizing composition.

18. The method of claim 1, wherein the contact comprises exposing the article to vapors of the sterilizing composition.

19. The method of claim 1, wherein the alcohol is selected from the group consisting of methanol, ethanol, n-propanol, isopropanol, benzyl alcohol, cresol and carbinol.

20. The method of claim 1, wherein the composition has a concentration of the alcohol between about 10 percent by weight and about 40 percent by weight.

21. The method of claim 1, wherein the composition comprises additional antimicrobial agents.

22. A method of treating an article comprising cross-linked tissue, the method comprising contacting the article with a sterilizing composition comprising an epoxy amine compound, the cross-linked tissue having been further processed prior to contact with sterilizing composition.

23. The method of claim 22, wherein the contact reduces the viable microbes associated with the article by about $1 \times 10^{-6}$.

24. The method of claim 22, wherein the cross-linked tissue has been further processed by treatment with an anti-calcification agent prior to contact with the sterilizing composition.

25. The method of claim 22, wherein the epoxy amine compound is triglycidyl amine.

26. The method of claim 22, wherein the articles are selected from the group consisting of heart valves, prosthesis and vascular grafts.

27. The method of claim 22, wherein the article further comprises synthetic materials.

28. The method of claim 22, wherein the tissue has been cross-linked with gluteraldehyde.

29. The method of claim 22, wherein the tissue has been cross-linked with epoxy amine compounds.

30. A method of treating a non-proteinaceous article, the method comprising contacting the article with a sterilizing composition comprising an epoxy amine compound.

31. The method of claim 30 wherein the epoxy amine compound is a polyepoxy amine compound.

32. The method of claim 30, wherein the articles are selected from the group consisting of surgical implements, dental implements, mechanical heart valves, bioreactors, containers, pipetmen, and tubing.

33. A sterilizing composition comprising an epoxy amine compound and an alcohol.

* * * * *